(12) United States Patent
Sinha et al.

(10) Patent No.: US 10,345,239 B1
(45) Date of Patent: Jul. 9, 2019

(54) THIN STACKUP FOR DIFFUSE FLUORESCENCE SYSTEM

(71) Applicant: Verily Life Sciences LLC, Mountain View, CA (US)

(72) Inventors: Supriyo Sinha, Menlo Park, CA (US); Seung Ah Lee, Menlo Park, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 0 days.

(21) Appl. No.: 15/678,513

(22) Filed: Aug. 16, 2017

Related U.S. Application Data (60) Provisional application No. 62/384,711, filed on Sep. 8, 2016.

(51) Int. Cl.
*G01N 21/64* (2006.01)

(52) U.S. Cl.
CPC ... *G01N 21/645* (2013.01); *G01N 2021/6471* (2013.01); *G01N 2201/062* (2013.01); *G01N 2201/0612* (2013.01); *G01N 2201/08* (2013.01)

(58) Field of Classification Search
CPC ......... G01N 21/645; G01N 2021/6471; G01N 2201/0612; G01N 2201/062; G01N 2201/08
See application file for complete search history.

(56) References Cited

U.S. PATENT DOCUMENTS

| | | | | |
|---|---|---|---|---|
| 4,818,710 A * | 4/1989 | Sutherland | ........... | G01N 21/648 250/227.23 |
| 4,832,815 A * | 5/1989 | Kambara | ........... | G01N 21/6428 204/612 |
| 5,062,942 A * | 11/1991 | Kambara | ........... | G01N 21/6456 204/612 |
| 5,268,080 A * | 12/1993 | Kambara | ......... | G01N 27/44782 204/461 |
| 5,307,148 A * | 4/1994 | Kambara | ............. | G01N 21/645 204/481 |
| 6,300,638 B1 * | 10/2001 | Groger | ................. | G01N 21/648 250/458.1 |
| 6,468,409 B1 * | 10/2002 | Asp | .................. | G01N 27/44721 204/452 |
| 6,515,743 B1 * | 2/2003 | Hayashi | ............. | G01N 21/6452 250/458.1 |
| 8,981,303 B2 * | 3/2015 | Ouchi | ................... | G01J 5/0818 250/353 |

(Continued)

*Primary Examiner* — Marcus H Taningco
(74) *Attorney, Agent, or Firm* — McDonnell Boehnen Hulbert & Berghoff LLP (57) ABSTRACT

The present disclosure relates to optical systems for fluorescence-based imaging. An example optical system includes an image sensor. The image sensor is sensitive to at least a first wavelength of light and a second wavelength of light. The optical system also includes a light guiding layer optically coupled to the image sensor and a light source positioned to emit light into a side surface of the light guiding layer. The emitted light includes light at the first wavelength and the emitted light is transmitted in an in-plane direction in the light guiding layer. The optical system further includes a thin film filter and an output coupler optically coupled to the light guiding layer. At least a portion of the emitted light transmitted in an in-plane direction in the light guiding layer is coupled out of the light guiding layer in an out-of-plane direction via the output coupler.

20 Claims, 6 Drawing Sheets (56) References Cited

U.S. PATENT DOCUMENTS

| | | | | |
|---|---|---|---|---|
| 2001/0003043 A1* | 6/2001 | Metspalu | ............ | G01N 21/6428 |
| | | | | 435/6.19 |
| 2004/0091862 A1* | 5/2004 | Brandenburg | ....... | C12Q 1/6837 |
| | | | | 435/6.19 |
| 2008/0095669 A1* | 4/2008 | Kang | ................. | G01N 21/6452 |
| | | | | 422/82.08 |
| 2008/0204753 A1* | 8/2008 | Ohtsuka | ............. | G01N 21/6428 |
| | | | | 356/417 |
| 2009/0321662 A1* | 12/2009 | Ohtsuka | ................. | G01N 21/05 |
| | | | | 250/459.1 |
| 2010/0152066 A1* | 6/2010 | Malik | .................. | B01L 3/5027 |
| | | | | 506/35 |
| 2013/0253338 A1* | 9/2013 | Kang | .................. | A61B 5/0071 |
| | | | | 600/477 |
| 2015/0268399 A1* | 9/2015 | Futterer | ................. | G02B 6/005 |
| | | | | 315/151 |

\* cited by examiner

Figure 1

Cross-Section View

Figure 2

Oblique View

Figure 3

Cross-Section View

Figure 4

Oblique View

THIN STACKUP FOR DIFFUSE FLUORESCENCE SYSTEM

CROSS-REFERENCE TO RELATED APPLICATIONS

The present application is a non-provisional patent application claiming priority to Provisional Patent Application No. 62/384,711, filed Sep. 8, 2016, the contents of which are hereby incorporated by reference.

BACKGROUND

Fluorescence imaging involves a fluorophore marker or tag that emits light at an emission wavelength in response to interacting with light at an excitation wavelength. Conventional fluorescence imaging systems may include optical arrangements such as off-axis illumination and folded illumination with a dichroic optical element. However, both approaches require considerable volume and thickness (along the optical axis) to separate light at the excitation and emission wavelengths. The off-axis illumination arrangement uses this volume and thickness to angularly separate the two wavelengths and the folded path arrangement uses a dichroic optical element, which may utilize considerable thickness along the optical axis.

SUMMARY

In one aspect, an optical system is provided. The optical system includes an image sensor and a light guiding layer optically coupled to the image sensor. The image sensor is sensitive to at least a first wavelength of light and a second wavelength of light. The optical system also includes a light source positioned to emit light into a side surface of the light guiding layer. The emitted light includes light at the first wavelength and the emitted light is transmitted in an in-plane direction in the light guiding layer. The optical system further includes an output coupler optically coupled to the light guiding layer. At least a portion of the emitted light transmitted in the in-plane direction in the light guiding layer is coupled out of the light guiding layer in an out-of-plane direction via the output coupler. The optical system yet further includes a thin film filter disposed between the light guiding layer and the image sensor. The thin film filter has a stopband and a passband. The stopband includes the first wavelength and the passband includes the second wavelength.

In another aspect, another optical system is provided. The optical system includes an image sensor and a light guiding layer optically coupled to the image sensor. The image sensor is sensitive to at least a first wavelength of light and a second wavelength of light. The light guiding layer has a conical frustum shape and includes an angled sidewall. The optical system includes a light source positioned to emit light toward the angled sidewall of the light guiding layer. The emitted light includes light at the first wavelength and the emitted light is transmitted in an in-plane direction in the light guiding layer after interacting with the angled sidewall. The optical system also includes an output coupler optically coupled to the light guiding layer. At least a portion of the emitted light transmitted in the in-plane direction in the light guiding layer is coupled out of the light guiding layer in an out-of-plane direction via the output coupler. The optical system yet further includes a thin film filter disposed between the light guiding layer and the image sensor. The thin film filter has a stopband and a passband. The stopband includes the first wavelength and the passband includes the second wavelength.

These as well as other embodiments, aspects, advantages, and alternatives will become apparent to those of ordinary skill in the art by reading the following detailed description, with reference where appropriate to the accompanying drawings. Further, it should be understood that this summary and other descriptions and figures provided herein are intended to illustrate embodiments by way of example only and, as such, that numerous variations are possible. For instance, structural elements and process steps can be rearranged, combined, distributed, eliminated, or otherwise changed, while remaining within the scope of the embodiments as claimed.

DETAILED DESCRIPTION

Example methods, devices, and systems are described herein. It should be understood that the words "example" and "exemplary" are used herein to mean "serving as an example, instance, or illustration." Any embodiment or feature described herein as being an "example" or "exemplary" is not necessarily to be construed as preferred or advantageous over other embodiments or features. Other embodiments can be utilized, and other changes can be made, without departing from the scope of the subject matter presented herein.

Thus, the example embodiments described herein are not meant to be limiting. Aspects of the present disclosure, as generally described herein, and illustrated in the figures, can be arranged, substituted, combined, separated, and designed in a wide variety of different configurations, all of which are contemplated herein.

Further, unless context suggests otherwise, the features illustrated in each of the figures may be used in combination with one another. Thus, the figures should be generally viewed as component aspects of one or more overall embodiments, with the understanding that not all illustrated features are necessary for each embodiment.

I. Overview

Optical fluorescence measurements in tissue may be challenging due to tissue scattering and absorption. For example, optical techniques that rely on ballistic photons for image generation (two-photon excitation microscopy, confocal microscopy, wide-field microscopy, etc.) are typically only able to image to a depth of about 0.5 mm to 1 mm. At depths greater than 1 mm, most photons have been scattered and thus provide only diffuse optical imaging results. However, it is desirable to image at depths of up to 2 mm, particularly with regard to wrist-mounted wearable devices that collect fluorescence emission light from a fluorophore of interest. A wearable form factor presents a challenge to optical systems because conventional methods of in-coupling excitation light and collection and detection of the fluorescence emission light may be difficult in a compact volume.

The present disclosure describes an optical system that may provide a very thin (e.g., several millimeters thick) optical stackup that incorporates both the excitation and collection optics. Specifically, the compact stackup includes illumination using edge coupled light sources such as one or more laser diodes or light emitting diodes (LEDs). Light emitted by the light source is coupled into a thin layer or film (about 1 mm thick or less) and may include an excitation wavelength. The excitation light is guided in this layer, at least in part, through total internal reflection (TIR). On one side of the light guiding layer, the TIR is frustrated so that a portion of the excitation light is scattered out and may be directed toward a sample (e.g., tissue). In an example embodiment, the excitation light may be scattered out of the film via an output coupler. The excitation light may interact with a fluorophore proximate to the sample (e.g., within the tissue). In an example embodiment, the fluorophore may emit light at an emission wavelength in response to the interaction with the excitation light. Some of the emission light is scattered back towards the film. The film transmits a significant portion of the emission light (either due to spectral discrimination due to a thin film on one side of the film or spatially where the film is not uniformly scattering or angularly). The emission light is then transmitted to an image sensor where it can be captured and quantified.

In an example embodiment, various aspects of the optical system may be selected based on the following considerations. First, it is desirable for the output coupler to provide light scattering along a relatively short optical throw length, such as the light coupling films used in conventional cell phone and notebook computer displays to provide light to the liquid crystal display (LCD) elements. However, these displays are typically many inches in linear dimension whereas present embodiments may provide that the light be scattered in less than one inch. Additionally, the light guiding film should allow a sufficient amount of fluorescence emission light to be transmitted for detection by the image sensor.

Second, it is desirable for the thickness of the system to be minimized so as to optimize spatial resolution and reduce wearable device size. With no lenses in the optical system, spatial resolution may degrade as the image sensor moves further away from the sample plane.

Third, it is desirable for the optical system to include a light-filtering element that stops light at the excitation wavelength from the reaching the image sensor, while allowing light at the emission wavelength to pass through to the image sensor.

Finally, it is desirable for the image sensor to have a low profile so that the image sensor and its accompanying readout circuitry do not add undue height to the optical system.

The optical system may include a variety of optical filtering elements that may be used to increase contrast between the excitation light and the fluorescence/emission light. For example, such optical filtering elements may include thin film filters, angular filters, brightness enhancement films, and/or optical polarizers.

The present disclosure may provide compact, lens-less diffuse fluorescence imagers for integration into wearable devices. Such compact imaging devices may also be utilized in general medical diagnostic devices.

II. Example Optical Systems

Figure 1:
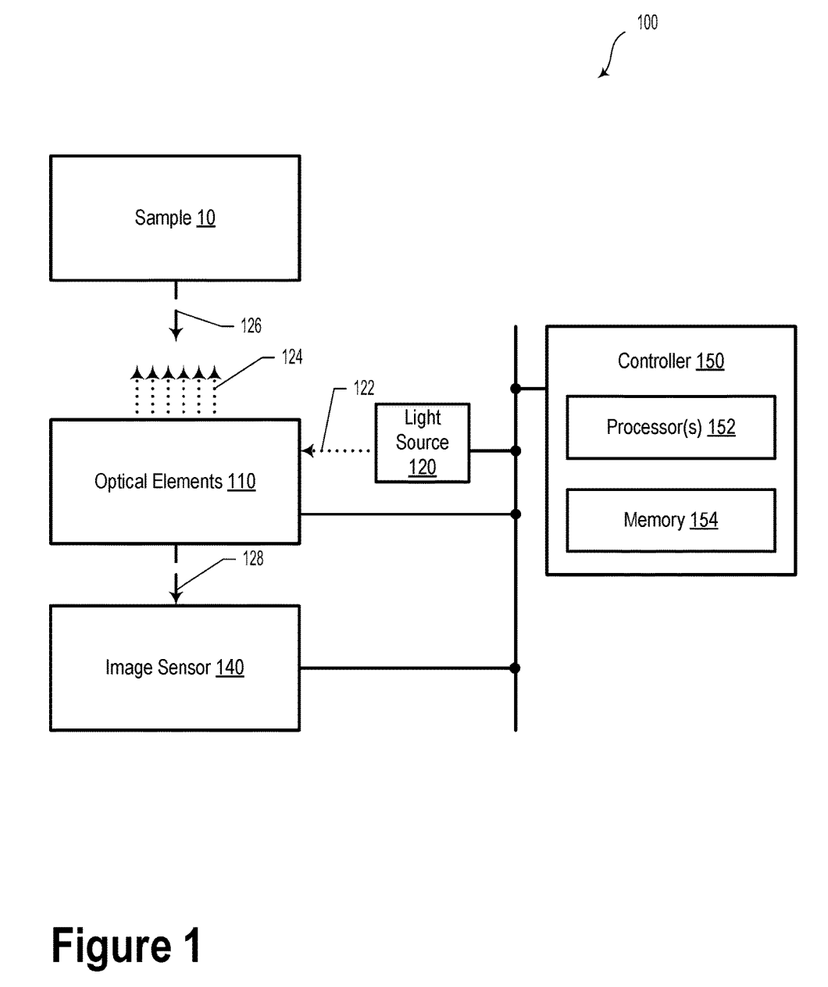
FIG. 1 is a schematic diagram of an optical system, according to an example embodiment.

FIG. 1 illustrates a schematic diagram of an optical system 100, according to an example embodiment. The optical system 100 includes optical elements 110, a light source 120, an image sensor 140, and a controller 150. In an example embodiment, the optical system 100 may be incorporated into a wearable device (e.g., a smartwatch, a patch, a bracelet, or a necklace). In another embodiment, the optical system 100 may be incorporated into a smartphone, tablet, laptop computer, or another type of computing device. Additionally or alternatively, the optical system 100 may take the form of another type of medical imaging system.

The optical elements 110 may include a "stackup" of one or more optical elements, which may include an angular filter, a light guiding layer, and/or a thin film filter. Other types of optical elements are contemplated within the scope of the present disclosure.

The light source 120 may include one or more laser diodes or LEDs that may emit excitation light 122. In an example embodiment, the excitation light 122 may be emitted toward at least a portion of the optical elements 110.

The optical elements 110 may transmit the excitation light 122 along an in-plane direction. In some embodiments, the excitation light 122 may be transmitted along the in-plane direction via total internal reflection in a light guiding layer.

In an example embodiment, the excitation light 122 may interact with an output coupler of the optical elements 110. The interaction with the output coupler may cause the excitation light to be directed in an out-of-plane direction, providing out-of-plane excitation light 124.

In some embodiments, the out-of-plane excitation light 124 may be incident upon a sample 10. The sample 10 may include one or more fluorophores. The fluorophores may absorb light energy of a specific wavelength and re-emit light at a longer wavelength. Namely, the fluorophores may emit emission light 126 in response to interacting with light at the excitation wavelength. In other words, emission light 126 may be produced based on an interaction between the fluorophores in sample 10 and the out-of-plane excitation light 124. Emission light 126 may be generally at a longer wavelength than excitation light 124. At least a portion of the optical elements 110 may be substantially transparent to the emission light 126. In such a scenario, at least a portion of emission light 126 may be transmitted through the optical elements 110 toward the image sensor 140 as incident emission light 128. The incident emission light 128 may be detected by the image sensor 140.

In an example embodiment, the image sensor 140 may include a charge-coupled device (CCD) or a complementary metal-oxide semiconductor (CMOS) image sensor. In some embodiments, the image sensor 140 may include a single photodetector (e.g., a single pixel photodiode) or several photodetectors (e.g., ten photodiodes) in a 1-D or 2-D arrangement. It is understood that the image sensor 140 may be operable to detect light in various spectral ranges such as the visible light spectrum, the near-infrared (NIR) wavelength range, mid-infrared (MIR) wavelength range and/or the long wavelength infrared (LWIR) range. The image sensor 140 may be operable to detect light in other spectral ranges.

Controller 150 may include at least one processor 152 and a memory 154. The memory 154 may include a non-transitory computer readable medium. Namely, the memory 154 may include read-only memory (ROM), random access memory (RAM), a floppy disk drive, a hard disk drive, a solid state drive (SSD), or another type of memory element configured to store information. The processor 152 may be configured to execute program instructions stored in memory 154 so as to carry out the operations described herein.

The controller 150 may be operable to control a variety of elements of optical system 100. For example, controller 150 may cause light source 120 to turn on or off. Additionally or alternatively, controller 150 may modulate an operating condition of light source 120. That is, controller 150 may cause the light source 120 to operating as a modulated light source. In an example embodiment, the controller 150 may modulate light source 120 so as to improve a signal-to-noise ratio (SNR).

Furthermore, the controller 150 may be operable to receive image information from the image sensor 140. As an example, still or video images captured via image sensor 140 may be saved in memory 154. The controller 150 may be additionally or alternatively configured to provide video or still-image processing. The controller 150 may be operable to carry out any number of other operations related to fluorescence imaging.

Figure 2:
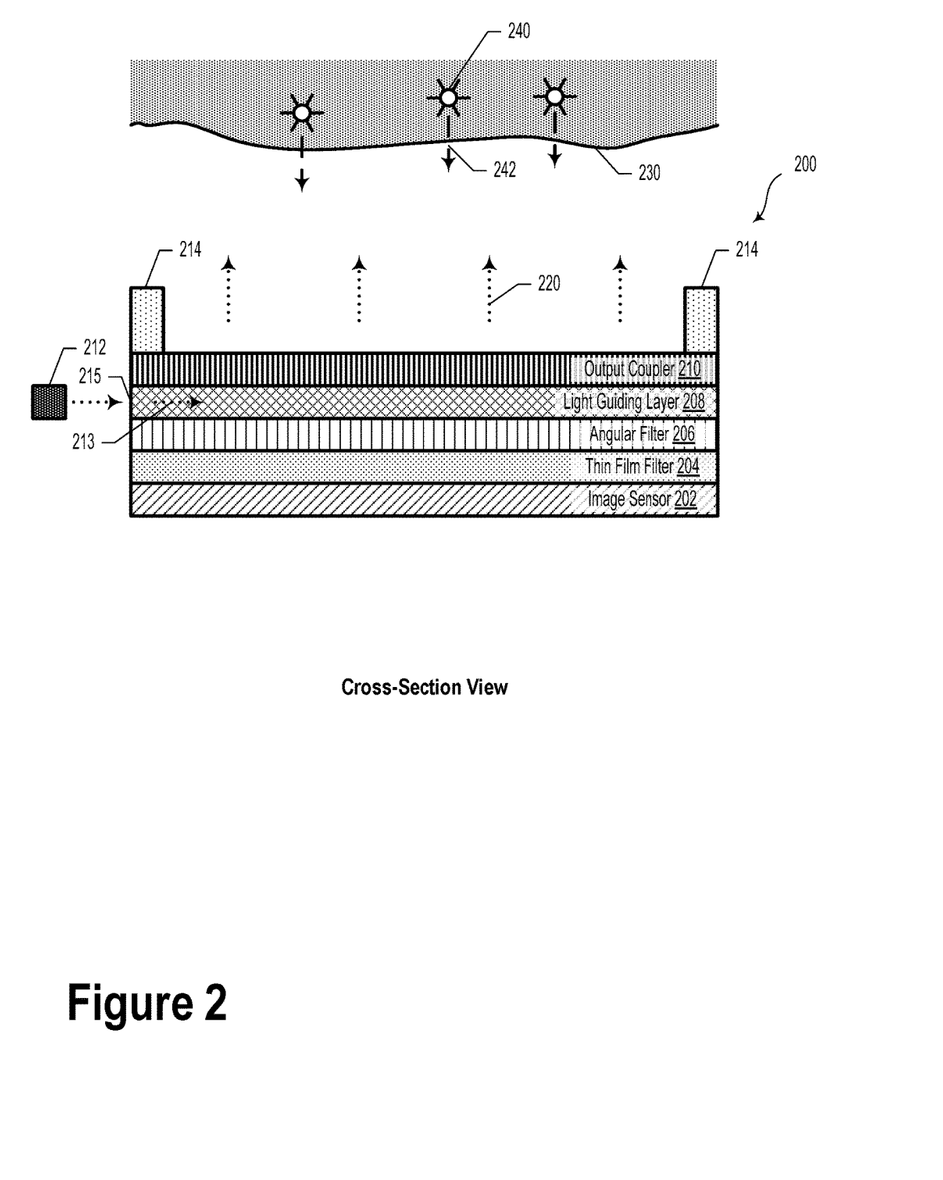
FIG. 2 illustrates an optical system, according to an example embodiment.

FIG. 2 illustrates a cross-sectional view of an optical system 200, according to an example embodiment. The optical system 200 may include similar or identical elements as those corresponding to optical system 100 as illustrated and described in reference to FIG. 1.

The optical system 200 may include an image sensor 202, a thin film filter 204, an angular filter 206, a light guiding layer 208, and an output coupler 210. The optical system 200 also includes a light source 212. Optionally, the optical system 200 may include a standoff 214.

The optical system 200 may include more or fewer optical elements. For example, in some embodiments, the angular filter 206 may be omitted. Furthermore, some of the optical elements described herein may be combined. For example, in some embodiments, the light guiding layer 208 and output coupler 210 may be combined in a single element. It is understood that many other such optical combinations and configurations are possible and contemplated herein.

The image sensor 202 may include, for example, a complementary metal oxide semiconductor (CMOS) image sensor or a charge-coupled device (CCD) image sensor. However, other types of image sensors are possible and contemplated. For instance, the image sensor 202 may include a photonic mixer device, a modulated image intensifier, a single photon avalanche detector (SPAD), or an array of SPAD detectors. Furthermore, in other embodiments, the image sensor 202 may include a single pixel detector.

In an example embodiment, the image sensor 202 is sensitive to at least a first wavelength of light and a second wavelength of light. Specifically, the first wavelength of light may include a wavelength of light emitted by the light source 212. In some embodiments, light having at first wavelength may be termed excitation light. Furthermore, the second wavelength of light could include a wavelength of light emitted by a fluorophore upon an interaction with the excitation light, which may be termed emission light.

In an embodiment, the thin film filter 204 may be disposed between the light guiding layer 208 and the image sensor 202. The thin film filter 204 may be a dichroic filter or reflector. That is, the thin film filter 204 may selectively pass or transmit certain wavelengths or wavebands of light while reflecting other wavelengths of light. Additionally or alternatively, the thin film filter 204 may be an absorptive filter. In some embodiments, the thin film filter 204 may include a dielectric stack of various materials (e.g., niobium pentoxide, silicon nitride, and/or silicon dioxide). In such scenarios, the dielectric stack may form a Bragg mirror or a one-dimensional photonic crystal.

In an example embodiment, the thin film filter 204 may include a spectral stopband and a spectral passband. The stopband may include the first wavelength of light (e.g., the excitation light) and the passband may include the second wavelength (e.g., the emission light). In some embodiments, the stopband of the thin film filter 204 may be characterized by an optical density (OD) of greater than three over the stopband. That is, the thin film filter 204 may transmit 0.1% or less of light within the stopband.

In some embodiments, the angular filter 206 may be disposed between the image sensor 202 and the light guiding layer 208. The angular filter 206 may selectively transmit light incident upon the angular filter 206 within a given angular range while rejecting (e.g., absorbing or reflecting) light incident at other angles. For example, the angular filter 206 may transmit light propagating through it at small angles near normal incidence (e.g., less than 5 to 10 degrees from normal incidence) while reflecting or absorbing light incident at other angles. In an example embodiment, the angular filter 206 may provide optical isolation between excitation light 213 emitted by the light source 212 and incident emission light 242. That is, the angular filter 206 may provide partial or complete rejection of the excitation light 213. Furthermore, the angular filter 206 may limit or restrict the angular range of light rays incident upon, or transmitted through, the thin film filter 204. As the thin film filter 204 may have angle-dependent filtering characteristics, the optical characteristics of system 200 may be more easily controlled or predicted by limiting the angular range of light incident upon or transmitted through the thin film filter 204. In such a scenario, a combination of the angular filter 206 and the thin film filter 204 may provide filtering of light based on its spectral and angular characteristics.

In an example embodiment, the angular filter 206 may include an array of holes with a predetermined aspect ratio, which may be based, for example, on a desired angular transmission range and/or a spectral transmission range. For example, the aspect ratio may be selected such that only light with certain incidence angles may be transmitted to the thin film filter 204. All other light may be substantially absorbed or reflected by the walls of the array. Although some embodiments contemplate that the holes of the angular filter 206 will transmit light with incident angles near normal incidence, other angle ranges are contemplated. That is, in some embodiments, the holes of the angular filter 206 may be tilted or otherwise arranged such that the transmitted range of angles is substantially non-normal.

The light guiding layer 208 may be optically coupled to the image sensor 202. The light guiding layer 208 may be formed from one or more optical materials, such as silica-based glass or plastic (e.g., polymethylmethacrylate or PMMA). In some embodiments, the light guiding layer 208 may include one or more dopants (e.g., erbium, germanium dioxide, or titanium). Additionally or alternatively, the light guiding layer 208 may include one or more optical fibers or photonic crystal materials. Other optical materials are contemplated in the present disclosure.

The light guiding layer 208 may provide a medium for excitation light 213 to be transmitted along an in-plane direction. In some embodiments, the excitation light 213 may propagate within the light guiding layer 208 via total internal reflection (TIR). That is, excitation light 213 propagating within the light guiding layer 208 may be entirely or substantially reflected from a boundary of the light guiding layer 208 if it is incident upon that surface at an angle greater than a critical angle $\theta_c$, which is given by the equation:

$$\theta_c = \arcsin\left(\frac{n_2}{n_1}\right),$$

where $n_1$ is the index of refraction of the light guiding layer 208 and $n_2$ is the index of refraction of the optical element beyond the boundary of the light guiding layer 208 (e.g., the angular filter 206, the thin film filter 204, or the output coupler 210).

The light source 212 may include one or more laser diodes and/or light emitting diodes (LEDs). Furthermore, the light source may be operable to emit excitation light 213 at a first wavelength (e.g., an excitation wavelength of a target fluorophore). In an example embodiment, the light source 212 may be operable to emit light at about a wavelength of 495 nm (e.g., at an excitation wavelength of fluorescein). However, emission of light at other wavelengths, specifically wavelengths of light that may excite fluorophores, is possible and contemplated herein. For example, the light source 212 may emit light at about 612 nm, which may be an excitation wavelength for a fluorescent dye such as Alexa Fluor 610.

In further embodiments, the light source 212 may provide a plurality of wavelengths of light. Additionally or alternatively, in the scenario where light source 212 includes a plurality of LEDs or laser diodes, the various light sources could be operable to provide different wavelengths of light.

In an example embodiment, the light source 212 may be positioned to emit light into a side surface 215 of the light guiding layer 208. For example, the light source 212 may include a plurality of LEDs disposed along a side surface 215 of the light guiding layer. As illustrated in FIG. 2, the light emitted from light source 212 may be transmitted in an in-plane direction in the light guiding layer 208. As described elsewhere herein, the excitation light 213 may be propagated within the light guiding layer 208, at least in part, via total internal reflection.

The output coupler 210 may be optically coupled to the light guiding layer 208. In an example embodiment, the output coupler 210 may include a grating or light scattering structure coupled to, or part of, a top surface of the light guiding layer 208. In some embodiments, the output coupler 210 may include a roughened surface. Additionally or alternatively, the output coupler 210 may include dimples, grooves, or other topographical structure or texture along a surface of an optical material. Yet further, the output coupler 210 may include one or more thin films configured to couple light out of the light guiding layer 208.

In such scenarios, at least a portion of the emitted light transmitted in an in-plane direction in the light guiding layer (e.g., excitation light 213) may be coupled out of the light guiding layer 208 in an out-of-plane direction (e.g., forming excitation light 220) via the output coupler 210. That is, the output coupler 210 may cause excitation light 220 to propagate toward a sample 230.

The sample 230 may be positioned relative to the output coupler 210 such that the emitted light coupled in the out-of-plane direction (e.g., excitation light 220) illuminates the sample 230. In an example embodiment, the sample includes a fluorophore 240 that provides emission light 242 at the second wavelength in response to excitation by light at the first wavelength (e.g., excitation light 220).

In some embodiments, optical system 200 may include a standoff 214 disposed proximate to an outer circumference of a top surface of the output coupler 210. In such embodiments, at least one dimension of the standoff 214 (e.g., a height of the standoff 214) may be selected based on a working distance of the optical system 200. The working distance of the optical system 200 may include a desired imaging arrangement of the optical system 200 with regard to a sample surface or subsurface features within the sample. In some embodiments, the working distance may correspond to a focal distance or a desired imaging distance. For example, if the working distance of the optical system 200 is determined to be 0.8 mm, the standoff 214 may correspond to that height so as to position the optical system 200 at the desired imaging arrangement with respect to a sample surface. Other sizes of standoff 214 are possible and contemplated. In some examples, standoff 214 may include a faceplate, a guard, and/or a protective coating.

Figure 3:
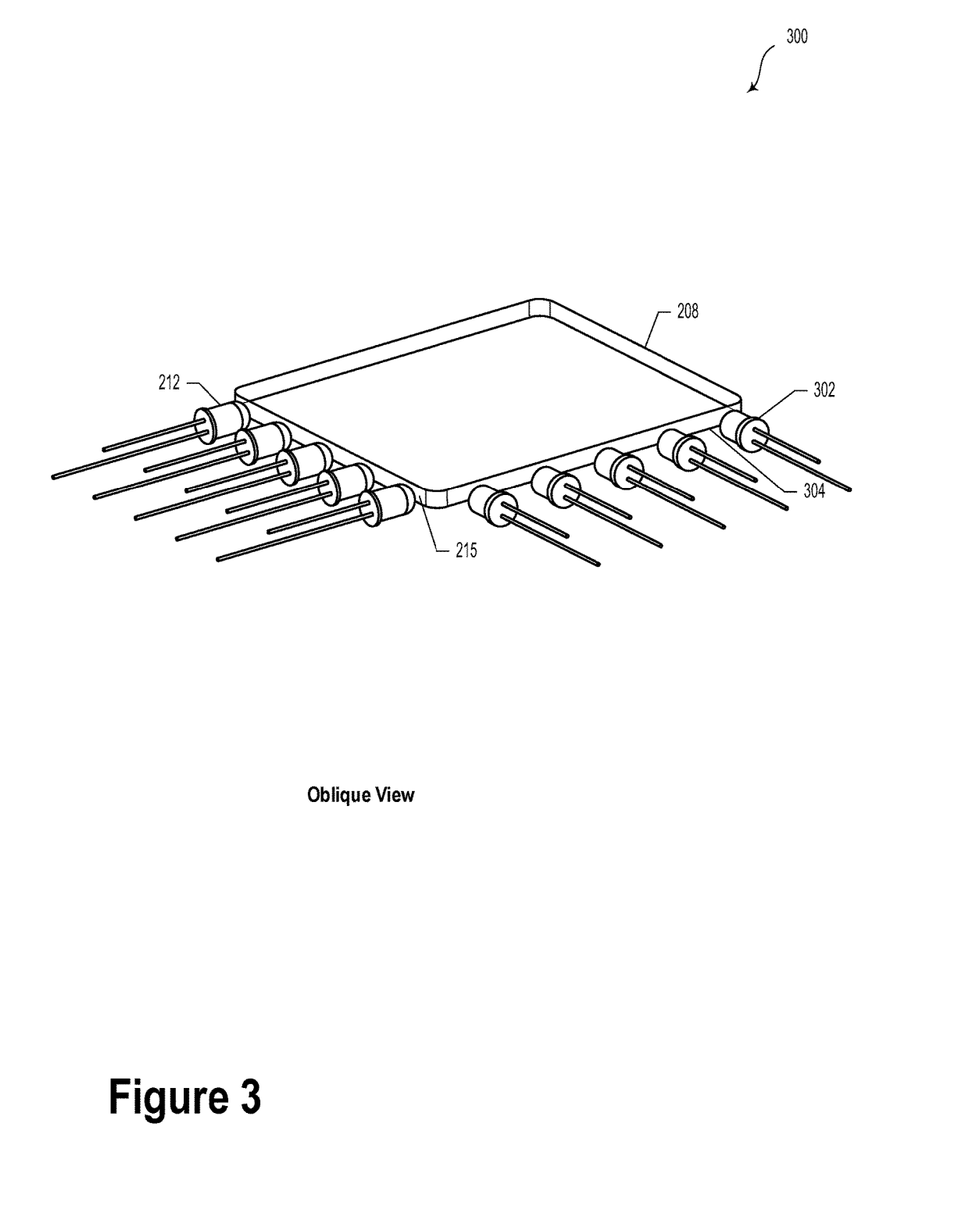
FIG. 3 illustrates a portion of an optical system, according to an example embodiment.

FIG. 3 illustrates a portion of an optical system 300, according to an example embodiment. The optical system 300 may include elements similar or identical to corresponding elements in optical systems 100 and 200 as illustrated and described in reference to FIGS. 1 and 2. As shown in FIG. 3, optical system 300 includes a first set of light sources 212 (e.g., LEDs) arranged along a first side surface 215 of light guiding layer 208 and a second set of light sources 302 arranged along a second side surface 304 of light guiding layer 208.

It is understood that other arrangements and configurations of optical systems 100, 200, and 300 are possible. For example, the light source 212 may include a third set of LEDs disposed along a third side surface of the light guiding layer 208. Yet further, the light source 212 may include a fourth set of LEDs disposed along a fourth side surface of the light guiding layer 208. Other orientations or arrangements of light source 212 are possible.

In an example embodiment, the light guiding layer 208 (and possibility one or more elements of optical system 300) may have a cylindrical shape. In such a scenario, the light source 212 may include a plurality of LEDs disposed proximate to the cylindrical sidewall of the light guiding layer 208.

Figure 4:
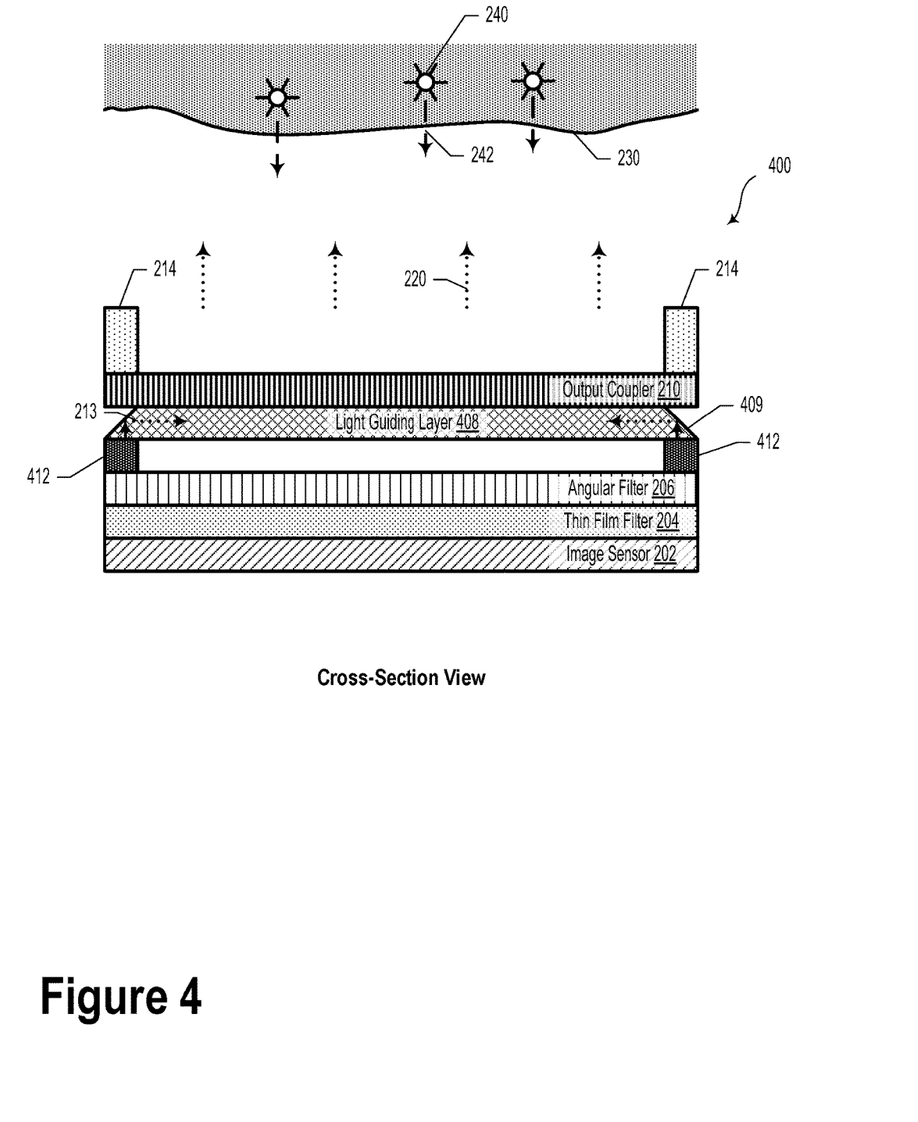
FIG. 4 illustrates an optical system, according to an example embodiment.

FIG. 4 illustrates an optical system 400, according to an example embodiment. The optical system 400 may include elements similar or identical to corresponding elements in optical systems 100, 200, and 300 as illustrated and described in reference to FIGS. 1, 2, and 3. However, optical system 400 may include a light guiding layer 408 that has a frustum shape with an angled sidewall 409. The frustum shape of the light guiding layer 408 could be, for example, a conical or pyramidal frustum shape. Alternatively, the light guiding layer 408 could have some other shape that provides an angled sidewall.

As shown in FIG. 4, a light source 412 may be positioned to emit light 409 toward the angled sidewall 409 of the light guiding layer 408. The emitted light includes light at the first wavelength (e.g., the excitation wavelength). The emitted light 213 may be transmitted in an in-plane direction in the light guiding layer 408 after interacting with the angled sidewall 409 (e.g., after reflection by the angled sidewall 409). In an example embodiment, the light source 412 may include a plurality of laser diodes or LEDs disposed proximate to an outer circumference of a bottom surface of the light guiding layer.

Figure 5:
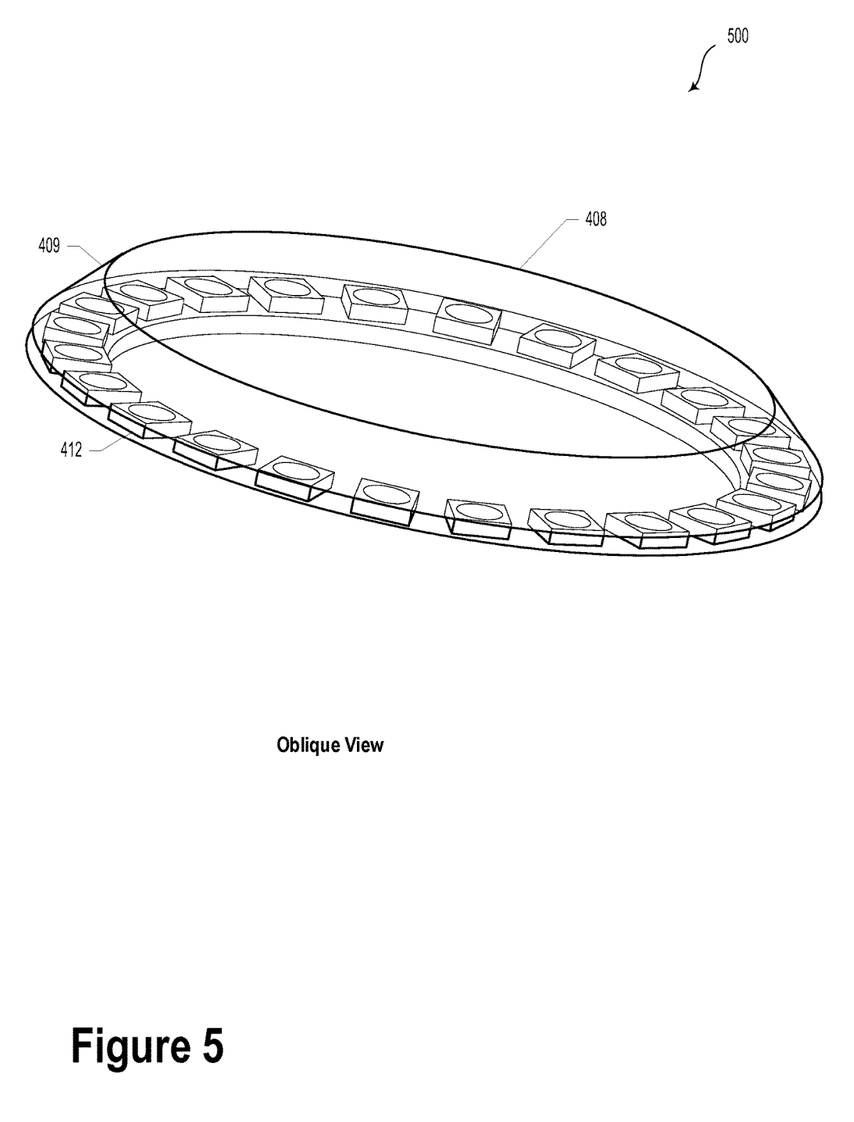
FIG. 5 illustrates a portion of an optical system, according to an example embodiment.

FIG. 5 illustrates a portion of an optical system 500, according to an example embodiment, which may be described as a ring-based LED system. As shown in FIG. 5, the LEDs are placed below the face of the light guiding layer 408. In this example, the frustum shape provides a 45-degree angled surface that is reflective (e.g., mirrored) to reflect the light along an in-plane direction towards the center of the light guiding layer. The ring of LEDs could also be placed around the light guiding layer, in which case the LEDs would emit light toward the center axis of the light guiding layer.

As illustrated in FIG. 5, the optical system 500 may include an annular or circular arrangement of LEDs that may be operable to emit light upward toward the angled sidewall 409 of the light guiding layer 408. Other arrangements of the light source 412 are contemplated with regard to the present disclosure.

While FIGS. 1-5 illustrate embodiments incorporating certain optical elements, it is understood that other optical elements may also be included. For example, optical diffusers, reflectors, and lenses are contemplated herein. Additionally or alternatively, an optical polarizer may be disposed between the light source and light guide to possibly improve signal to noise ratio (SNR). In such a scenario, it may be possible to efficiently discriminate between polarized excitation light and unpolarized fluorescence emission light (e.g., in the case where the angular filter 206 or thin film filter 204 is a polarizing filter).

In an example embodiment, an overall height of the optical systems 100, 200, 300, 400, or 500 may be less than a few millimeters. For example, an overall height of the optical system could be 3 mm or less.

Figure 6:
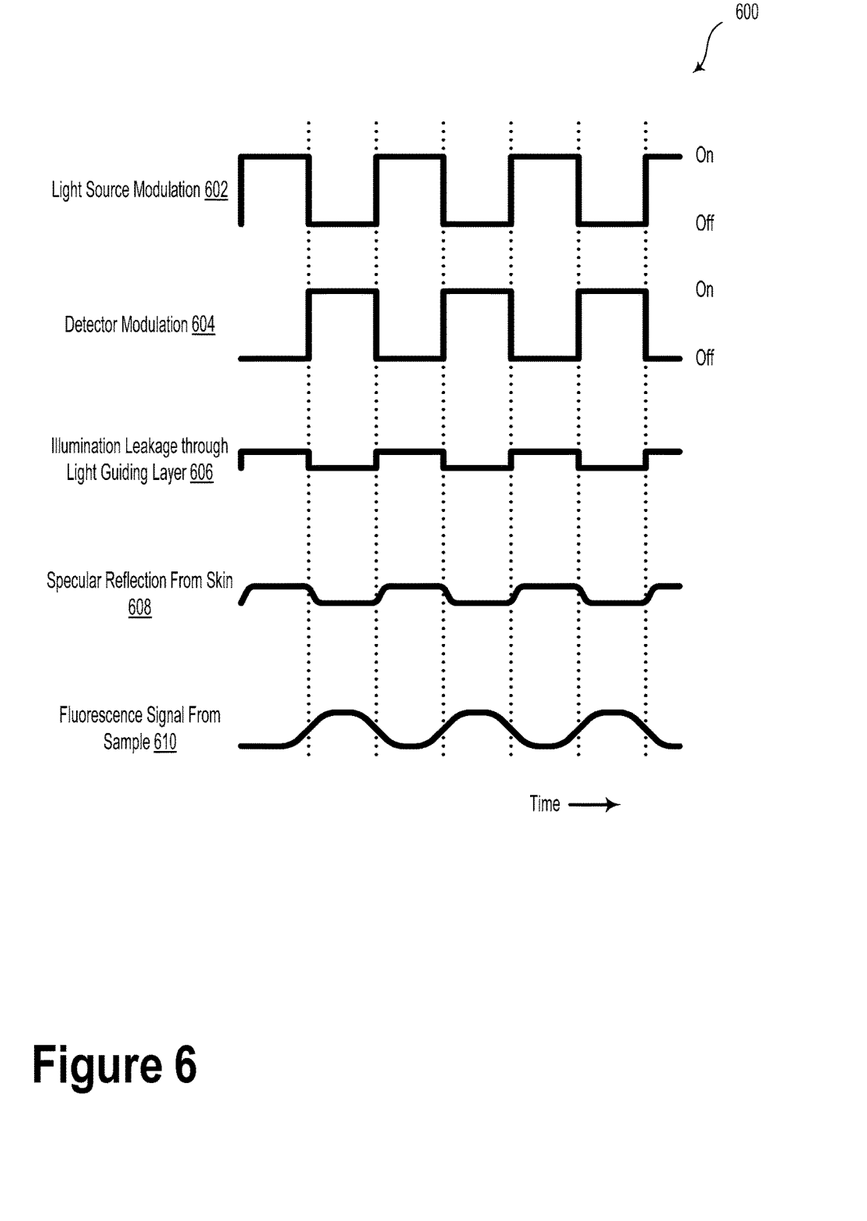
FIG. 6 illustrates several optical waveforms, according to an example embodiment.

FIG. 6 illustrates several optical waveforms 600, according to an example embodiment. The optical waveforms 600 may represent various optical signals over time. The optical waveforms 600 may be provided in the optical systems 100, 200, 300, 400, or 500, as illustrated and described in relation to FIGS. 1-5.

In an embodiment, the illumination source and the detector may be modulated at the same frequency but with a 180 degree phase shift. In such a scenario, the time-delayed fluorescence signal from deep tissue or long-life time fluorescence dyes may be detected more easily and/or efficiently.

In some embodiments, the phase shift could be less than 180 degrees. For example, if the illumination source is operated with a duty cycle of less than 50%, the phase shift could vary depending at least on the duty cycle. In such a scenario, the illumination source and the image sensor or detector may be modulated so as to minimize temporal overlap between illumination time and fluorescence signal and/or to maximize the signal to noise ratio of the fluorescence signal.

For example, light source 120 may be modulated by controller 150, which may provide light source modulation waveform 602. That is, controller 150 may modulate one or more light emitters of light source 120 between an on state and an off state.

Furthermore, one or more detectors of image sensor 140 may be modulated by controller 150, which may provide detector modulation 604. In such a scenario, image sensor 140, or a portion thereof, may be modulated between an on (e.g., detecting) state and an off (e.g., non-detecting) state. In other embodiments, a detector gain setting of the image sensor 140 may be modulated. As such, one or more detectors of image sensor 140 need not be "switched off", but the effective gain level could be reduced as so as to eliminate any potential photosignal.

Some of the light emitted by light source 120 may "leak" or propagate through a bottom surface of the light guiding layer as illustrated in waveform 606. In such cases, the stray light could be filtered by the angular filter 206 and/or the thin film filter 204.

Furthermore, some excitation light may be reflect from a surface of the sample (e.g., a skin surface), as illustrated in waveform 608. Additionally, a fluorescence signal 610 could be produced based on light emitted from the sample (e.g., due to excitation of a fluorophore). Thus, as shown in FIG. 6, the light source modulation 602 and the detector modulation 604 may be such that the image sensor is off when the light source is on and such that the image sensor is on when the light source is off and the fluorescence signal 610 is maximal. Furthermore, as described herein, the light source modulation 602 and detector modulation 604 may be controlled temporally (independently and/or with respect to one another) so as to maximize detection of the fluorescence signal 610, which may correspond to maximizing a signal to noise ratio of the fluorescence signal 610.

The modulated detectors may include photonic mixer devices, modulated image intensifiers, single photon avalanche diodes (SPAD) or SPAD array detectors. Furthermore, the modulation frequency, f could be selected such that the time delay between the illumination leakage (both specular reflection and direct leakage from the light guiding layer) and the fluorescence signal is in the order of 1/f. Such a time delay may result from differences in propagation distance due to multiple light scattering events in a tissue sample (e.g., in deep tissue imaging). The time delay may also result from long-lifetime fluorescence dyes, such as in fluorescence lifetime imaging (FLIM). In both cases, the time delay may be on the order of nanoseconds, which can be detectable on the order of few 10s of MHz to GHz modulation.

Accordingly, modulation techniques using modulated illumination and modulated detectors may provide better rejection of the specularly reflected light if scattering in the tissue and excitation light leakage is significant. Such modulation techniques may improve the SNR of imaging techniques that utilize optical systems 100, 200, 300, 400, and 500.

The particular arrangements shown in the Figures should not be viewed as limiting. It should be understood that other embodiments may include more or less of each element shown in a given Figure. Further, some of the illustrated elements may be combined or omitted. Yet further, an illustrative embodiment may include elements that are not illustrated in the Figures.

A step or block that represents a processing of information can correspond to circuitry that can be configured to perform the specific logical functions of a herein-described method or technique. Alternatively or additionally, a step or block that represents a processing of information can correspond to a module, a segment, or a portion of program code (including related data). The program code can include one or more instructions executable by a processor for implementing specific logical functions or actions in the method or technique. The program code and/or related data can be stored on any type of computer readable medium such as a storage device including a disk, hard drive, or other storage medium.

The computer readable medium can also include non-transitory computer readable media such as computer-readable media that store data for short periods of time like register memory, processor cache, and random access memory (RAM). The computer readable media can also include non-transitory computer readable media that store program code and/or data for longer periods of time. Thus, the computer readable media may include secondary or persistent long term storage, like read only memory (ROM), optical or magnetic disks, compact-disc read only memory (CD-ROM), for example. The computer readable media can also be any other volatile or non-volatile storage systems. A computer readable medium can be considered a computer readable storage medium, for example, or a tangible storage device.

While various examples and embodiments have been disclosed, other examples and embodiments will be apparent to those skilled in the art. The various disclosed examples and embodiments are for purposes of illustration and are not intended to be limiting, with the true scope being indicated by the following claims.

What is claimed is:

1. An optical system, comprising:
    an image sensor, wherein the image sensor is sensitive to at least a first wavelength of light and a second wavelength of light;
    a light guiding layer optically coupled to the image sensor;
    a light source positioned to emit light into a side surface of the light guiding layer, wherein the emitted light includes light at the first wavelength, and wherein the emitted light is transmitted in an in-plane direction in the light guiding layer;
    an output coupler optically coupled to the light guiding layer, wherein at least a portion of the emitted light transmitted in the in-plane direction in the light guiding layer is coupled out of the light guiding layer in an out-of-plane direction via the output coupler; and
    a thin film filter disposed between the light guiding layer and the image sensor, wherein the thin film filter has a stopband and a passband, wherein the stopband includes the first wavelength and the passband includes the second wavelength.

2. The optical system of claim 1, wherein the image sensor comprises one or more photodetectors.

3. The optical system of claim 1, wherein the image sensor comprises at least one of: a complementary metal oxide semiconductor (CMOS) image sensor, a charge-coupled device (CCD) image sensor, a photonic mixer device, a modulated image intensifier, a single photon avalanche detector (SPAD), or an array of SPAD detectors.

4. The optical system of claim 1, further comprising an angular filter disposed between the image sensor and the light guiding layer.

5. The optical system of claim 1, further comprising a standoff disposed proximate to an outer circumference of a top surface of the output coupler, wherein at least one dimension of the standoff is selected based on a working distance of the optical system.

6. The optical system of claim 1, wherein the light source comprises at least one of a laser diode or a light emitting diode (LED).

7. The optical system of claim 1, wherein the light source comprises a first plurality of light emitting diodes (LEDs) disposed along a first side surface of the light guiding layer.

8. The optical system of claim 1, wherein the light source further comprises a second plurality of LEDs disposed along a second side surface of the light guiding layer.

9. The optical system of claim 1, wherein the light source further comprises a third plurality of LEDs disposed along a third side surface of the light guiding layer and a fourth plurality of LEDs disposed along a fourth side surface of the light guiding layer.

10. The optical system of claim 1, wherein the light guiding layer has a cylindrical shape and comprises a sidewall, wherein the light source comprises a plurality of LEDs disposed proximate to the sidewall of the light guiding layer.

11. The optical system of claim 1, wherein the emitted light coupled in the out-of-plane direction illuminates a sample.

12. The optical system of claim 11, wherein the sample comprises a fluorophore that emits light at the second wavelength in response to excitation by light at the first wavelength.

13. An optical system, comprising:
    an image sensor, wherein the image sensor is sensitive to at least a first wavelength of light and a second wavelength of light;
    a light guiding layer optically coupled to the image sensor, wherein the light guiding layer has a conical frustum shape and comprises an angled sidewall;
    a light source positioned to emit light toward the angled sidewall of the light guiding layer, wherein the emitted light includes light at the first wavelength, and wherein the emitted light is transmitted in an in-plane direction in the light guiding layer after interacting with the angled sidewall;
    an output coupler optically coupled to the light guiding layer, wherein at least a portion of the emitted light transmitted in the in-plane direction in the light guiding layer is coupled out of the light guiding layer in an out-of-plane direction via the output coupler; and
    a thin film filter disposed between the light guiding layer and the image sensor, wherein the thin film filter has a stopband and a passband, wherein the stopband includes the first wavelength and the passband includes the second wavelength.

14. The optical system of claim 13, wherein the image sensor comprises one or more photodetectors.

15. The optical system of claim 13, wherein the image sensor comprises at least one of: a complementary metal oxide semiconductor (CMOS) image sensor, a charge-coupled device (CCD) image sensor, a photonic mixer device, a modulated image intensifier, a single photon avalanche detector (SPAD), or an array of SPAD detectors.

16. The optical system of claim 13, further comprising an angular filter disposed between the image sensor and the light guiding layer.

17. The optical system of claim 13, further comprising a standoff disposed proximate to an outer circumference of a top surface of the output coupler, wherein at least one dimension of the standoff is selected based on a working distance of the optical system.

18. The optical system of claim 13, wherein the light source comprises a plurality of laser diodes or light emitting diodes (LEDs) disposed proximate to an outer circumference of a bottom surface of the light guiding layer.

19. The optical system of claim 13, wherein the emitted light coupled in the out-of-plane direction illuminates a sample.

20. The optical system of claim 19, wherein the sample comprises a fluorophore that emits light at the second wavelength in response to excitation by light at the first wavelength.

* * * * *